United States Patent
Wallace

(10) Patent No.: US 7,067,510 B2
(45) Date of Patent: Jun. 27, 2006

(54) DIHYDRO-DIBENZO[B,E]OXEPINE BASED SELECTIVE ESTROGREN RECEPTOR MODULATORS, COMPOSITIONS AND METHODS

(75) Inventor: Owen Brendan Wallace, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/521,137

(22) PCT Filed: Jul. 11, 2003

(86) PCT No.: PCT/US03/19554

§ 371 (c)(1),
(2), (4) Date: Jan. 12, 2005

(87) PCT Pub. No.: WO2004/009603

PCT Pub. Date: Jan. 29, 2004

(65) Prior Publication Data

US 2005/0240017 A1    Oct. 27, 2005

Related U.S. Application Data

(60) Provisional application No. 60/398,538, filed on Jul. 24, 2002.

(51) Int. Cl.
| | |
|---|---|
| A61K 31/55 | (2006.01) |
| A01N 43/00 | (2006.01) |
| C07D 223/14 | (2006.01) |
| C07D 331/02 | (2006.01) |
| C07D 313/00 | (2006.01) |

(52) U.S. Cl. ................. 514/213.01; 514/215; 514/431; 514/443; 540/576; 549/1; 549/354

(58) Field of Classification Search ................ 540/576; 549/1, 354; 514/215, 213.01, 431, 443, 450
See application file for complete search history.

(56) References Cited

FOREIGN PATENT DOCUMENTS

| | | | |
|---|---|---|---|
| EP | 0761669 | * | 2/1996 |
| EP | 0 761669 | | 9/1996 |
| EP | 0 943329 | | 3/1999 |

OTHER PUBLICATIONS

Grese, et al., Synthesis and Pharmacology of Conformationally Restricted Raloxifene Analogues: Highly Potent Selective Estrogen Receptor Modulators, *J. Med. Chem,* 1998, vol. 41, pp. 1272-1283.

* cited by examiner

*Primary Examiner*—D. Margaret Seaman
*Assistant Examiner*—Niloofar Rahmani
(74) *Attorney, Agent, or Firm*—John C. Demeter; Gilbert T. Voy

(57) ABSTRACT

The present invention provides a compound of the formula (I) wherein $R^1$ is —H, —OH, —O($C_1$-$C_4$ alkyl), —OCOC$_6$H$_5$, —OCO($C_1$-$C_6$ alkyl), or —OSO$_2$($C_2$-$C_6$ alkyl); $R^0$, $R^2$ and $R^3$ are each independently —H, —OH, —O($C_1$-$C_4$ alkyl), —OCOC$_6$H$_5$, —OCO($C_1$-$C_6$ alkyl), —OSO$_2$($C_2$-$C_6$ alkyl) or halo; R4 is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino; n is 2 or 3; X is —S— or —HC=CH—; G is —O—, —S—, —SO—, SO$_2$, or —N($R^5$)—, wherein $R^5$ is —H or $C_1$-$C_4$ alkyl; and Y is —O—, —S—, —NH—, —NMe-, or —CH$_2$—; or a pharmaceutically acceptable salt thereof; pharmaceutical compositions thereof, optionally in combination with estrogen and progestin; methods of inhibiting a disease associated with estrogen deprivation; and methods for inhibiting a disease associated with an aberrant physiological response to endogenous estrogen.

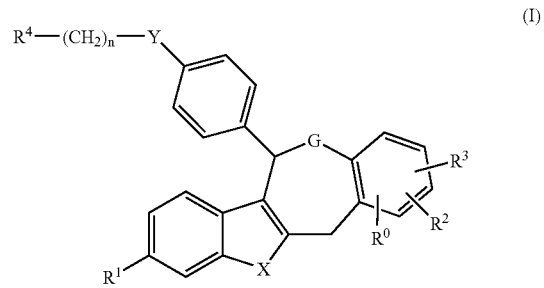

18 Claims, No Drawings

DIHYDRO-DIBENZO[B,E]OXEPINE BASED SELECTIVE ESTROGREN RECEPTOR MODULATORS, COMPOSITIONS AND METHODS

This application claims the benefit under 35 U.S.C. §120 of International Application No. PCT/US2003/019554 filed Jul. 11, 2003, which claims the benefit under 35 U.S.C. § 119(e) of U.S. Ser. No. 60/398,538, filed Jul. 24, 2002.

BACKGROUND OF THE INVENTION

The present invention relates to pentacyclic oxepines and derivatives thereof, compositions containing those compounds, their use as selective estrogen receptor modulators, and their use in inhibiting bone loss, cardiovascular disease, and breast and uterine carcinoma.

Menopause, the transition in women from the reproductive to the non-reproductive stage of life, is characterized by the cessation of menstruation and occurs at an average age of fifty years. The postmenopausal state is characterized by changes in the levels of circulating sex hormones, the most dramatic of which is the reduction in plasma levels of 17β-estradiol to less than ten percent of premenopausal values. Clinical and epidemiological studies have shown that the postmenopausal state is an important risk factor for a number of chronic disorders, notably osteoporosis and cardiovascular disease. In view of the fact that the current life span of women is about eighty years, women spend approximately one-third of their lives in the postmenopausal state. This means that the potential for chronic effects of the postmenopausal state on women's health is greater today than at the turn of the century when life expectancy was considerably shorter.

Osteoporosis describes a group of diseases which are characterized by the net loss of bone mass per unit volume. The consequence of this loss of bone mass and resulting bone fracture is the failure of the skeleton to provide adequate structural support for the body. The most vulnerable bone tissue to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the biomechanical strength of the overall structure.

Following the cessation of menses, most women lose from about 20% to about 60% of the bone mass in the trabecular compartment of the bone within 3 to 6 years. This rapid loss is generally associated with an increase of bone resorption and formation. However, the resorptive cycle is more dominant and the result is a net loss of bone mass.

In postmenopausal osteoporosis, it is primarily the net resorption and loss of the trabeculae which leads to the failure and fracture of bone. In light of the loss of the trabeculae in postmenopausal women, it is not surprising that the most common fractures are those associated with bones which are highly dependent on trabecular support, for example the vertebrae, the neck, and the weight bearing bones such as the femur and the fore-arm. Indeed, hip fracture, collies fractures, and vertebral crush fractures are hallmarks of postmenopausal osteoporosis.

There are an estimated 25 million women in the United States alone who are afflicted with this disease. The results of osteoporosis are personally harmful and also account for a large economic loss due its chronicity and the need for extensive and long term support (hospitalization and nursing home care). This is especially true in more elderly patients. Additionally, although osteoporosis is not generally thought of as a life threatening condition, a 20% to 30% mortality rate is related with hip fractures in elderly women. A large percentage of this mortality rate can be directly associated with postmenopausal osteoporosis.

Cardiovascular disease is the leading cause of death among women. Compared to men, premenopausal women are relatively protected from cardiovascular disease; however, this protection is gradually lost following menopause. The nature of estrogen's ability to regulate serum lipids is not well understood, but evidence indicates that estrogen can up-regulate the low density lipid (LDL) receptors in the liver which act to remove excess cholesterol. Additionally, estrogen appears to have some effect on the biosynthesis of cholesterol, and other beneficial effects on cardiovascular health.

At the present time, one generally accepted method for treatment of disorders resulting in the postmenopausal state from the decline in estrogen levels is estrogen replacement therapy. The therapy may take the form of administering estrogen alone in so-called unopposed estrogen replacement therapy (ERT) or in the form of coadministering estrogen and progestin in a so-called hormonal replacement therapy (HRT) regimen. There are, however, major liabilities associated with chronic administration of estrogen in postmenopausal women having to do with adverse effects on the breast and uterus. Women on ERT develop endometrial cancer at rates three to six times higher than nonusers after three to six years of use; after ten years of ERT, the risk ratio increases to tenfold.

To combat these deleterious effect of ERT, the coadministration of progestin along with estrogen in a combined hormonal replacement therapy (HRT) is employed, since progestin acts to limit uterine stimulation and thus reduce the risk of uterine cancer.

Because of these known and suspected or feared liabilities of estrogen therapy, prescription of and patient compliance with chronic estrogen replacement therapy has been poor. It has been estimated that, in the United States among postmenopausal women for whom ERT or HRT has been prescribed, fewer than forty percent continue therapy beyond one year.

As a consequence, there is a need for the development of postmenopausal therapy agents which possess the ideal pharmacological profile: for example agents which produce the beneficial effects of estrogen upon skeletal tissue and the cardiovascular system without producing the adverse effects of estrogen upon the breast and the uterus. Agents possessing such an estrogen profile would reverse the effects of estrogen deficiency in certain tissues while at the same time bypassing or failing to act in tissues in which estrogen produces adverse effects. The term selective estrogen receptor modulators or "SERMs" has been applied such compounds which possess this tissue selective profile. SERMs are defined as compounds producing estrogen agonism in one or more desired target tissues such as bone, liver, etc., together with estrogen antagonism and/or minimal (i.e. clinically insignificant) agonism in reproductive tissues such as the breast or uterus.

BRIEF SUMMARY OF THE INVENTION

The present invention provides a compound of the formula

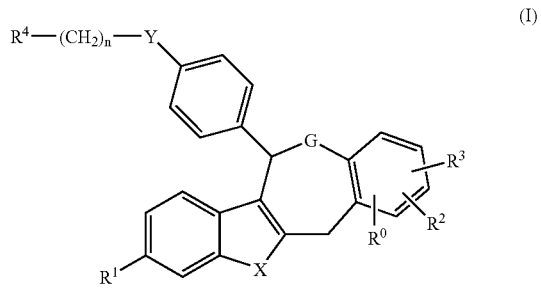

(I)

wherein $R^1$ is —H, —OH, —O($C_1$–$C_4$ alkyl), —OCO$C_6$H$_5$, —OCO($C_1$–$C_6$ alkyl), or —OSO$_2$($C_2$–$C_6$ alkyl);

$R^0$, $R^2$ and $R^3$ are each independently —H, —OH, —O($C_1$–$C_4$ alkyl), —OCO$C_6$H$_5$, —OCO($C_1$–$C_6$ alkyl), —OSO$_2$($C_2$–$C_6$ alkyl) or halo;

$R^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;

n is 2 or 3;

X is —S— or —HC=CH—;

G is —O—, —S—, —SO—, SO$_2$, or —N($R^5$)—, wherein $R^5$ is —H or $C_1$–$C_4$ alkyl; and Y is —O—, —S—, —NH—, —NMe-, or —CH$_2$—;

or a pharmaceutically acceptable salt thereof.

In a second embodiment, the present invention provides a pharmaceutical composition comprising a therapeutically effective amount of a compound of formula (I), alone or in combination with estrogen or progestin, and a pharmaceutically acceptable carrier.

In a further embodiment, the present invention provides medical methods of employing compounds of the present invention, for alleviating symptoms of estrogen deprivation, including bone loss, for example, osteoporosis; cardiovascular disease, for example hypertension, thrombosis and lowering serum cholesterol.

In an alternative embodiment of the medical method of the present invention, the compounds of the present invention are employed in the treatment of disease conditions associated with an aberrant physiological response to endogenous estrogen including uterine fibroid disease or uterine fibrosis, endometriosis, and estrogen dependent cancers.

In a still further embodiment, the invention relates to chemical intermediates used in synthesizing the compounds of Formula (I).

DETAILED DESCRIPTION OF THE INVENTION

General terms used in the description of compounds herein described bear their usual meanings. For example, "$C_1$–$C_6$ alkyl" refers to straight, branched, or cyclic aliphatic chains of 1 to 6 carbon atoms including moieties such as methyl, ethyl, propyl, isopropyl, butyl, n-butyl, pentyl, isopentyl, hexyl, isohexyl, cyclohexyl and the like. Likewise, "$C_1$–$C_4$ alkyl" refers to straight, branched, or cyclic aliphatic chains of 1 to 4 carbon atoms including moieties such as methyl, ethyl, propyl, isopropyl, butyl, n-butyl, cyclopropyl, and the like. Similarly, the term "$C_1$–$C_4$ alkoxy" represents a $C_1$–$C_4$ alkyl group attached through an oxygen molecule and include moieties such as, for example, methoxy, ethoxy, n-propoxy, isopropoxy, and the like.

The term "NMe" refers to methylamino. The term "halo" refers to bromo, chloro, fluoro and iodo.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "fracemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The designation "▬" refers to a bond that protrudes forward out of the plane of the page.

The designation "......" refers to a bond that protrudes backward out of the plane of the page.

The designation "⟿" refers to a bond wherein the stereochemistry is not defined.

As used herein, the term "estrogen" includes steroidal compounds having estrogenic activity such as, for example, 17β-estradiol, estrone, conjugated estrogen (Premarin®), equine estrogen 17a-ethynyl estradiol, and the like. As used herein, the term "progestin" includes compounds having progestational activity such as, for example, progesterone, norethylnodrel, nongestrel, megestrol acetate, norethindrone, and the like.

Preferred compounds of this invention include compounds of formula I wherein Y is —O—. Other preferred compounds of this invention include compounds of formula I wherein G is —O— or —S—.

Certain $R^3$ and $R^4$ groups also demonstrate preferable characteristics. For example, those compounds of formula I wherein $R^4$ is 1-pyrrolidinyl, 1-hexamethyleneimino, or 1-piperidinyl are preferred. A further preferred subgroup of the preferred 1-pyrrolidinyl, 1-hexamethyleneimino, or 1-piperidinyl compounds include those compounds wherein $R^1$, $R^2$, and $R^3$ are each independently —H, —OH or —OCH$_3$.

Although the free-base or acid forms of formula I compounds can be used in the methods of the present invention, it is preferred to prepare and use a pharmaceutically acceptable salt form. Thus, the compounds used in the methods of this invention form pharmaceutically acceptable acid or base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfueric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

Typical bases used to form pharmaceutically acceptable addition salts would be inorganic bases, such as, sodium hydroxide, potassium hydroxide, alkali carbonates or bicarbonates, calcium carbonate, magnesium carbonate, and the like. Additionally, organic bases may be utilized to form addition salts, e.g., alkyl amines, such as, triethylamine, dimethylamine, i-propylamine, and the like.

The pharmaceutically acceptable acid or base addition salts are typically formed by reacting a compound of formula I with an equimolar or excess amount of acid or base. The reactants are generally combined in a mutual solvent such as diethyl ether or ethyl acetate. The salt normally precipitates out of solution within about one hour to 10 days and can be isolated by filtration or the solvent can be stripped off by conventional means.

Specific examples of compounds contemplated as falling within the scope of the present invention include, but are not limited to the following compounds and their pharmaceutically acceptable salts:

5-[4-(2-piperidin-1-yl-ethoxy)-phenyl]-5,11-dihydro-6-oxa-12-thia-dibenzo[a,f]azulen-2-ol;

5-[4-(2-pyrrolidin-1-yl-ethoxy)-phenyl]-5,11-dihydro-6-oxa-12-thia-dibenzo[a,f]azulen-2-ol;

13-[4-(2-piperidin-1-yl-ethoxy)-phenyl]-7,13-dihydro-12-oxa-benzo[4,5]cyclohepta[1,2-a]naphthalen-3-ol; and 13-[4-(2-pyrrolidin-1-yl-ethoxy)-phenyl]-7,13-dihydro-12-oxa-benzo[4,5]cyclohepta[1,2-a]naphthalen-3-ol.

The compounds of formula (I) can be prepared by utilizing procedures and techniques well known and appreciated by one of ordinary skill in the art. A general synthetic scheme for preparing compounds of formula (I) wherein X is —S— is set forth in Scheme A, wherein all substituents, unless otherwise indicated, are previously defined.

SCHEME A

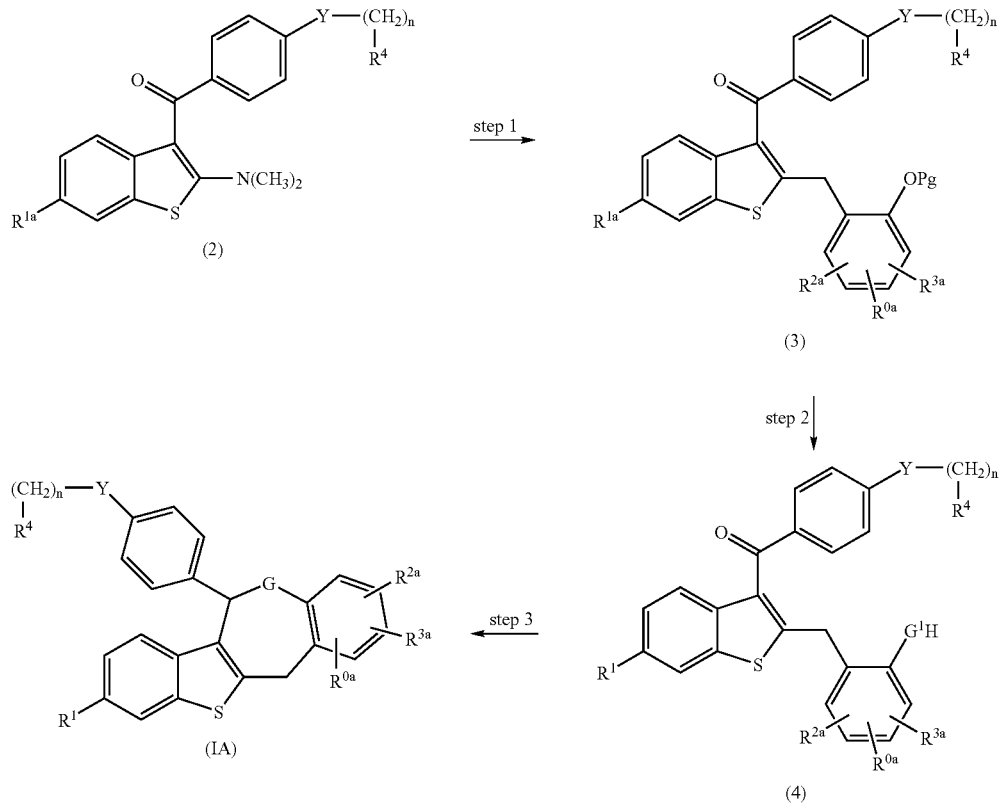

In Scheme A, $R^{0a}$, $R^{1a}$, $R^{2a}$, and $R^{3a}$ are each independently —H or —OPg, where Pg is a hydroxy protecting group and $R^{0a}$, $R^{2a}$ and $R^{3a}$ can further be halo. In compounds of formula (2), (3), et seq., the Pg protecting groups $R^{0a}$, $R^{1a}$, $R^{2a}$, and $R^{3a}$ are phenolic protecting groups of the type taught by T. Greene, et al. in Chapter 3 of "Protective Groups in Organic Synthesis," Second Edition, John Wiley & Sons, Inc., New York, 1991, pp. 143–170. The preferred protecting groups are alkyl ether groups, with methyl being particularly preferred. In Scheme A, the substituent $G^1$ is —O—, —S—, or —N($R^5$)—.

In Scheme A, step 1, the 6-methoxy-2-(2-methoxy-benzyl)-benzo[b]thiophene of formula (3) is prepared by reacting a dimethlyaminobenzothiophene of formula (2) with a suitably protected 2-alkoxybenzylmagnesium chloride under Grignard conditions, where Pg is a phenol protecting group such as a methyl or benzyl ether. The Grignard reactions are of the type taught by Godfrey (U.S. Pat. No. 5,420,349).

For example, the dimethylaminobenzothiophene (2) is reacted with a suitable 2-methoxybenzylmagnesium chloride under anhydrous conditions in a suitable aprotic organic solvent such as anhydrous tetrahydrofuran. The 2-methoxybenzylmagnesium chloride is preferably present in the reaction zone in a molar excess to dimethylaminobenzothiophene (2) of about 1.1 to about 3 equivalents. The reaction is carried out at a suitable temperature, preferably at room temperature, for a period of time ranging from about 1 to about 12 hours. The reaction is then quenched with a proton source such as, for example, sodium bicarbonate or methanol. The solvent is removed and the resulting mixture may be extracted, concentrated and purified according to techniques well known in the art, and the crude 6-substituted-2-(2-methoxy-benzyl)-benzo[b]thiophene (3) product may be used without further purification. For compounds of structure IA where G is S or N($R^5$), the preferred Pg is benzyl so that it may be removed by treating with $H_2$ on Pd/C without effecting the other methyl-protected phenol.

Appropriate dimethylaminobenzothiophenes (2) are known in the art, Grese et al., *J. Med. Chem.* 40(2), 146–147 (1997), U.S. Pat. No. 5,466,810 issued Nov. 14, 1995, U.S. Pat. No. 5,420,349 issued May 30, 1995, U.S. Pat. No. 5,792,870, issued Aug. 11, 1998, and U.S. Pat. No. 5,554,755, issued Sep. 10, 1996, or are prepared by techniques and procedures well known in the art.

In Scheme A, step 2, 2-(2-$G^1$H-benzyl)-benzo[b]thiophene (4) is prepared by deprotecting 6-substituted-2-(2-methoxy-benzyl)-benzo[b]thiophene (3) with a suitable deprotecting agent. The resulting alcohol functionality may then be converted when a thiol or amine is desired.

For example, 6-substituted-2-(2-methoxy-benzyl)-benzo[b]thiophene (3) is dissolved in a suitable organic solvent such as methylene chloride. In order to minimize side reactions during the $BBr_3$ deprotection, the HCl salt is first formed. The solution is contacted with excess HCl/ether to form the hydrochloric acid salt 6-substituted-2-(2-methoxy-benzyl)-benzo[b]thiophene (3). The solution is then concentrated to dryness and re-dissolved in the organic solvent. The solution is then cooled to a temperature ranging from about −10° C. to about 0° C. and a suitable deprotecting agent such as $BBr_3$ or sodium ethanthiolate (NaSEt) in an amount of about 1.1 to about 5 equivalents is added. Generally, the reaction requires 1 to 72 hours. For compounds where G is O, the 2-(2-G¹H-benzyl)-benzo[b]thiophene (4) can be isolated and purified by techniques well known in the art, such as extraction, evaporation, trituration, chromatography, and recrystallization, or phenol of formula (4) may be used without further purification. For compounds where G is S or N(R⁵), the benzyl protecting group of (3) is removed by treatment with hydrogen gas using a palladium on carbon catalyst. For compounds where G is S, the phenol of formula (4) is converted into the corresponding thiophenol using procedures known in the art such as initial conversion to the triflate followed by a palladium-mediated coupling with sodium triisopropylsilane thiolate (Arnould et al. Tetrahedron Lett. 1996, 37, 4523). Reduction of the ketone with LAH affords the corresponding alcohol. For compounds where G is N(R⁵), the phenol of formula (4) is converted to the corresponding amine using methods well known in the art, such as initial conversion to the triflate followed by a palladium-mediated coupling reaction (for example, Buchwald et al. Tetrahedron Lett. 1997, 38, 6367). The amine is then subjected to an intramolecular reductive amination using an acid source and reducing agent such as NaCNBH₃ or Na(OAc)₃BH. Where R⁵ is not H, the nitrogen may be alkylated using an alkyl halide and base, such as KOBu-t in THF.

In Scheme A, step 3, the cyclized product of formula (IA) is prepared by reducing 2-(2-G¹H-benzyl)-benzo[b]thiophene (4) and subjecting the reduced product to an acid-catalyzed cyclization.

For example, 2-(2-G¹H-benzyl)-benzo[b]thiophene (4) is contacted with an excess of a suitable reducing agent, such as diisobutylaluminum hydride (DIBAL), lithium aluminum hydride (LAH), aluminum hydride or borane dimethyl sulfide complex. The reaction is carried out in a suitable solvent, such as tetrahydrofuran or diethyl ether. The reaction is typically carried out at temperatures of from 0° C. to the refluxing temperature of the solvent. Typically, the reaction requires from about 15 minutes to about 36 hours. The reduced product is then contacted with a suitable acid, such as trifluoroacetic acid (TFA). The reaction is then heated gently for a period of time ranging from about 15 minutes to about 12 hours. The cyclized product of formula (IA) can be isolated and purified by techniques well known in the art, such as extraction, evaporation, trituration, chromatography, and recrystallization.

For compounds of formula (IA) where G is S or N(R⁵), when a hydroxy group is desired at R¹, R², and/or R³, a compound of formula (IA) is deprotected with a suitable deprotecting agent such as BBr₃, or sodium ethanthiolate (NaSEt). The BBr₃ reaction is conveniently carried out in a suitable organic solvent such as dichloromethane or dichloroethane while the NaSEt reaction can be conveniently carried out in DMF, THF, or N-methylpyrrolidinone (NMP). The reaction is quenched with water and diluted with a suitable organic solvent such as methylene chloride. The deprotected product where R⁰, R¹, R², and/or R³ are hydroxy can be isolated and purified by techniques well known in the art, such as extraction, evaporation, trituration, chromatography, and recrystallization.

A general synthetic scheme for preparing compounds of formula (1) wherein X is —CH=CH— is set forth in Scheme B, wherein all substituents, unless otherwise indicated, are previously defined.

SCHEME B

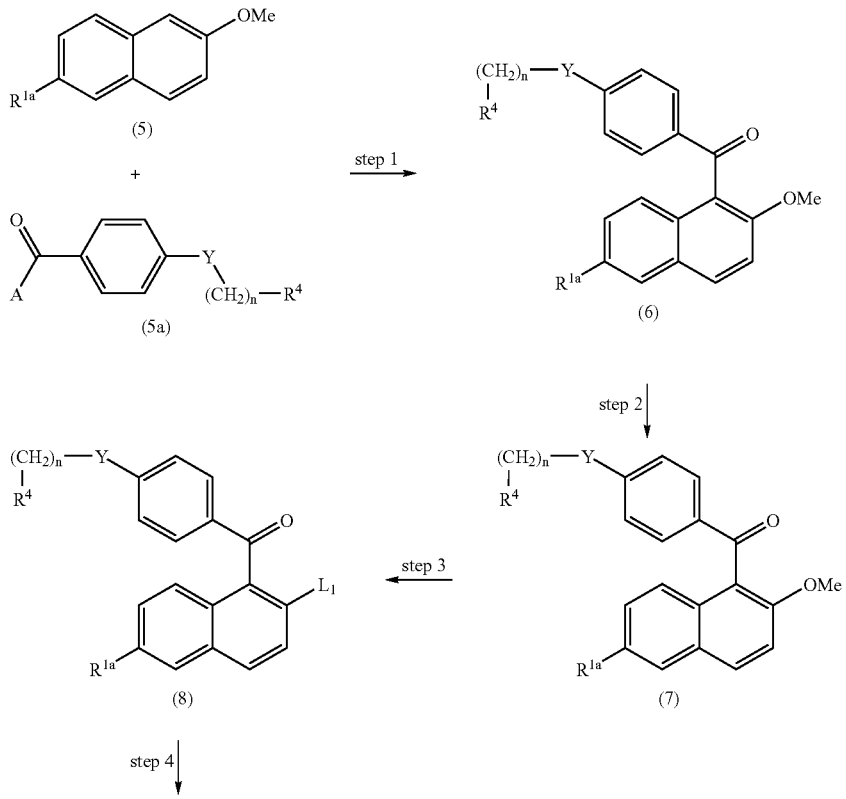

-continued

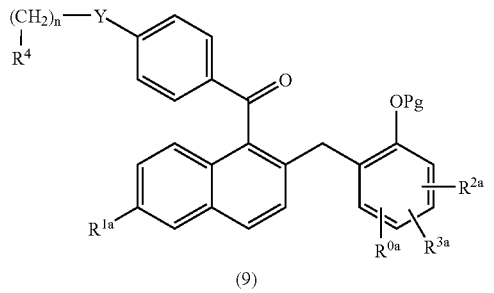

(9)

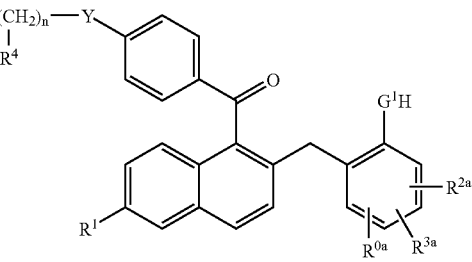

(10)

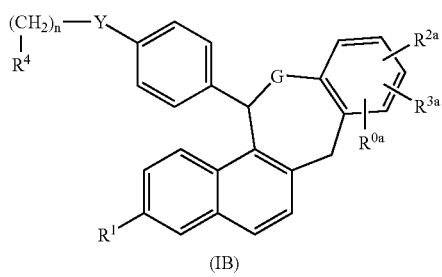

(IB)

step 5 → step 6 ↓ step 7 ←

(CH$_2$)$_n$—Y
|
R$^4$

OH

G$^1$H

R$^1$

R$^{2a}$

R$^{0a}$ R$^{3a}$ (11)

In Scheme B, R$^{0a}$, R$^{1a}$, R$^{2a}$, and R$^{3a}$ are each independently —H or —OPg, where Pg is a hydroxy protecting group and R$^0$, R$^{2a}$ and R$^{3a}$ can further be halo. En compounds of formula (5), (6), et seq., the Pg protecting groups R$^{0a}$, R$^{1a}$, R$^{2a}$, and R$^{3a}$ are phenolic protecting groups capable of withstanding the conditions of the Friedel-Crafts acylation reaction and are of the type taught by T. Greene, et al. in Chapter 3 of "Protective Groups in Organic Synthesis," Second Edition, John Wiley & Sons, Inc., New York, 1991, pp. 143–170. The preferred protecting groups are alkyl ether groups, with methyl being particularly preferred. In Scheme B, the substituent G$^1$ is —O—, —S—, or —N(R$^5$)—.

The activating group, A, is selected from groups well known in the art to activate acids for the purposes of carrying out Friedel-Crafts acylation reactions and include the acid halides, such as fluoride, chloride and bromide; mixed acid anhydrides with $C_1$–$C_6$ alkanoic acids; $C_1$–$C_6$ alkylsulfonic acids, arylsulfonic acids, perfluorinated $C_1$–$C_6$ alkanoic acids, $C_1$–$C_6$ alkylcarbonates, arylcarbonates, and the like. The preferred compounds of formula (8a) are those in which A is halogen, most preferably chlorine.

In Scheme B, step 1, a substituted naphthyl methanone of formula (6) is prepared by conducting a Friedel-Crafts acylation of a substituted naphthyl of formula (5) with a substituted benzoyl derivative of formula (5a).

For example, the acylation reaction between (5) and (5a) is carried out in an inert organic solvent in the presence of a Lewis acid catalyst. Suitable solvents include halogenated hydrocarbons such as dichloromethane, chloroform, 1,2-dichloroethane, carbon tetrachloride, chlorobenzene, dichlorobenzene and the like. The amount of solvent is not critical, but is generally sufficient to enable efficient mixing of the reaction components. Suitable Lewis acid catalysts for the Friedel-Crafts acylation reaction between (5) and (5a) include anhydrous aluminum, boron, or zinc halides with aluminum chloride being preferred. Temperature and time of reaction will vary, depending upon the choice of reaction solvent, Lewis acid catalyst, and activating group, A. Generally, reactions are carried out at temperatures below or at ambient to below or at the reflux temperature of the solvent. Reaction times vary from several minutes to about forty-eight hours. The progress of the reaction toward completion can be followed by well-known techniques such as thin-layer chromatographic analysis of aliquots of the reaction mixture during the course of the reaction.

Typically, the reaction is conducted using 1.0 to 1.5 equivalents of compound (5a) for each equivalent of compound (5), with more of the activated benzoyl compound added during the course of the reaction as needed to drive the reaction to completion. The amount of Lewis acid catalyst employed ranges from between about 0.1 to about 5 equivalents. The substituted naphthyl methanone of formula (6) can be isolated and purified by techniques well known in the art, such as extraction, evaporation, trituration, chromatography, and recrystallization.

Appropriate substituted benzoyl derivatives of formula (5a) can be prepared as described herein from its appropriate benzoic acid derivative as set forth analogously in U.S. Pat. No. 5,962,475, the disclosure of which is hereby incorporated by reference.

Appropriate benzoic acid derivatives of compounds of formula (5a) are set forth in U.S. Pat. No. 4,418,068, U.S. Pat. No. 5,631,369, and U.S. Pat. No. 5,852,193, the disclosures of which are hereby incorporated by reference.

In Scheme B, step 2, the 2-hydroxy-6-substituted-naphthalen-1-yl-methanone of formula (7) is prepared by selectively deprotecting the substituted naphthyl methanone of formula (6).

For example, the naphthyl methanone of formula (6) is reacted with a demethylation reagent such as boron tribromide, boron trichloride, or boron triiodide, or with AlCl$_3$.

The reaction is conducted under an inert atmosphere such as nitrogen, with one or more moles of the reagent per mole of methoxy group to be demethylated.

Appropriate solvents for this reaction are those solvents or mixture of solvents which remain inert throughout the demethylation reaction. Halogenated solvents such as dichloromethane, 1,2-dichloroethane, chloroform, methylene chloride, or aromatic solvents such as benzene or toluene are preferred. The temperature employed in this reaction of the present process should be sufficient to effect completion of the demethylation reaction. However, it is advantageous to keep the temperature below 0° C. in order to maximize selectivity for demethylation of the desired methoxy group and avoid the formation of undesirable by products, especially the dihydroxy analog arising from excessive demethylation. Under the preferred reaction conditions, a selectively dealkylated product will be formed after stirring the reaction for about 1 to 24 hours. After quenching the reaction, the 2-hydroxy-6-substituted-naphthalen-1-yl-methanone of formula (7) can be isolated and purified by techniques well known in the art, such as extraction, evaporation, trituration, chromatography, and recrystallization.

In Scheme B, step 3, a 2-L-substituted-6-substituted-naphthalen-1-yl-methanone of formula (8) is prepared by converting the hydroxy group of the 2-hydroxy-6-substituted-naphthalen-1-yl-methanone of formula (7) to an appropriate activating group.

An appropriate activating group, $L_1$, is one which is compatible with palladium-mediated coupling conditions and can be displaced by a 2-alkoxybenzylzinc halide of the formula

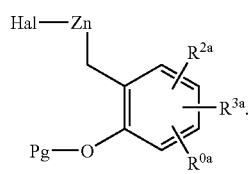

(8a)

where Hal is a halo group, preferably chloro. Appropriate activating groups, $L_1$, include bromo, iodo, and most preferably trifluoromethansulfonate.

For example, compounds in which $L_1$ is trifluoromethansulfonate are formed by contacting an appropriate 2-hydroxy-6-substituted-naphthalen-1-yl-methanone of formula (7) with a molar excess of trifluoromethanesulfonyl chloride. The reaction is carried out in a suitable solvent, such as dichloromethane, chloroform, toluene, benzene, or pyridine. The reaction is carried out in the presence of a suitable base, such as triethylamine, diisopropylethyl amine, or pyridine. Generally the reaction is carried out at temperatures of from −20° C. to 50° C. Generally, the reactions require from 30 minutes to 24 hours, The product can be isolated and purified by techniques well known in the art, such as extraction, evaporation, trituration, chromatography, and recrystallization.

In Scheme B, step 4, a [6-substituted-2-(substituted-benzyl)-naphthalen-1-yl]-[4-substituted-phenyl]-methanone of formula (9) may be prepared by coupling 2-L-substituted-6-substituted-naphthalen-1-yl-methanone of formula (8) to a 2-alkoxybenzylinc halide of formula (8a) using standard palladium-mediated coupling procedures [see, e.g., Knochel et al. Org. Lett. 1999, 1, 1323)].

For example, a slight excess of 2-alkoxybenzylzinc halide (8a) is added with each equivalent of 2-L-substituted-6-substituted-naphthalen-1-yl-methanone of formula (8) in the presence of a palladium catalyst and an appropriate base in an inert solvent, such as toluene, N-methylpyrrolidinone/toluene, or 1,2-dimethoxyethane. Although various palladium catalysts drive such coupling reactions, the catalyst selected is usually reaction-specific. The use of a bis(dibenzylideneacetone)palladium —Pd(dba)$_2$ catalyst in the present reaction is a preferred catalyst. Tetrabutylammonium iodide (Bu4NI) as an additive has been shown to improve yields and reaction times of similar couplings (Knochel et al. Org. Lett. 1999, 1, 1323). The temperature employed in this step should be sufficient to effect completion of the coupling reaction. Typically, gently heating the reaction mixture for a period from about 2 to about 8 hours is adequate. The product (9) can be isolated and purified by techniques well known in the art, such as extraction, evaporation, trituration, chromatography, and recrystallization.

Compounds of formula (8a) are either commercially available or derived from commercially available compounds via procedures well known to one of ordinary skill in the art [see, e.g., Advanced Organic Chemistry: Reactions, Mechanisms, and Structure, Fourth Edition, 3–16, (J. March, ed., John Wiley & Sons, Inc. 1992)].

In Scheme B, step 5, [6-substituted-2-(G$^1$H-benzyl)-naphthalen-1-yl]-[4-substituted-phenyl]-methanone (10) is prepared by deprotecting [6-substituted-2-(substituted-benzyl)-naphthalen-1-yl]-[4-substituted-phenyl]-methanone (9) with a suitable deprotecting agent according to procedures set forth in Scheme A, step 2. For compounds where G is S or N(R$^5$), the alcohol product of formula (10) can be converted to either the corresponding thiol or amine according to procedures set forth previously in Scheme A, step 2.

In Scheme B, step 6, [6-substituted-2-(G$^1$H-benzyl)-naphthalen-1-yl]-[4-substituted-phenyl]-methanol (11) is prepared by reducing the methanone of formula (10).

For example, a [6-substituted-2-(G$^1$H-benzyl)-naphthalen-1-yl]-[4-substituted-phenyl]-methanone (10) is reacted with an appropriate reducing agent, such as an alkali metal hydride, preferably lithium aluminum hydride. The reaction is carried out in a suitable solvent, such as tetrahydrofuran. The reaction is generally carried out at a temperature of from 0° C. to the refluxing temperature of the solvent. Generally, the reactions require from 30 minutes to 72 hours. The [6-substituted-2-(G$^1$H-benzyl)-naphthalen-1-yl]-[4-substituted-phenyl]-methanol (11) can be isolated and purified by techniques well known in the art, such as extraction, evaporation, trituration, chromatography, and recrystallization.

In Scheme B, step 7, the cyclized product of formula (IB) is prepared by subjecting [6-substituted-2-(GH-benzyl)-naphthalen-1-yl]-[4-substituted-phenyl]-methanol (11) to an acid-catalyzed cyclization.

For example, [6-substituted-2-(G$^1$H-benzyl)-naphthalen-1-yl]-[4-substituted-phenyl]-methanol (11) is diluted with a suitable solvent or solvent mixture, such as tetrahydrofuran and water followed by the addition of a suitable acid, such as hydrochloric acid. The reaction mixture is then heated gently for a period of time ranging from about 5 to 30 minutes, diluted with a suitable organic solvent, such as methylene chloride, and quenched with a suitable base, such as sodium carbonate, sodium bicarbonate, potassium carbonate, or potassium dicarbonate. The cyclized product of formula (IB) can be isolated and purified by techniques well known in the art, such as extraction, evaporation, trituration, chromatography, and recrystallization.

When a hydroxy group is desired at $R^0$, $R^1$, $R^2$, and/or $R^3$, a compound of formula (IB) can be deprotected, isolated and purified according to procedures set forth previously in Scheme A.

When a —OC(O)($C_1$–$C_6$ alkyl) or —OC(O)$C_6H_5$ group is desired at $R^0$, $R^1$, $R^2$, and/or $R^3$ a mono-, di-, or trihydroxy compound of formula, I, is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The acylation reactions which provide the aforementioned $R^0$, $R^1$, $R^2$, and/or $R^3$ groups are carried out at moderate temperatures in the range from about −25° C. to about 100° C., frequently under an inert atmosphere such as nitrogen gas. However, ambient temperature is usually adequate for the reaction.

Such acylations of the hydroxy group also may be performed by acid-catalyzed reactions of the appropriate carboxylic acids in inert organic solvents or neat. Acid catalysts such as sulfuric acid, polyphosphoric acid, methanesulfonic acid, and the like are used.

The aforementioned $R^0$, $R^1$, $R^2$, and/or $R^3$ groups also may be provided by forming an active ester of the appropriate acid, such as the esters formed by such known reagents as dicyclohexylcarbodiimide, acylimidazoles, nitrophenols, pentachlorophenol, N-hydroxysuccinimide, and 1-hydroxy-benzotriazole. See, e.g., *Bull. Chem. Soc. Japan*, 38:1979 (1965), and *Chem. Ber.*, 788 and 2024 (1970).

When a compound is desired in which $R^0$, $R^1$, $R^2$, and/or $R^3$ are —$OSO_2$($C_4$–$C_6$ alkyl), the suitable starting mono-, di- or trihydroxy compound is reacted with, for example, a derivative of the appropriate sulfonic acid such as a sulfonyl chloride, bromide, or sulfonyl ammonium salt, as taught by King and Monoir, *J. Am. Chem. Soc.*, 97:2566–2567 (1975). The mono-, di- or trihydroxy compound also can be reacted with the appropriate sulfonic anhydride. Such reactions are carried out under conditions such as were explained above in the discussion of reaction with acid halides and the like.

Compounds of formula (I) can be prepared so that $R^0$, $R^1$, $R^2$, and/or $R^3$ are different biological protecting groups or, preferably, the same biological protecting group. Preferred protecting groups include —$CH_3$, —C(O)C($CH_3$)$_3$, —C(O)$C_6H_5$, and —$SO_2$($CH_2$)$_3CH_3$.

Compounds of formula (5a) wherein Y is —S—, —NH—, —NMe-, or $H_2$— may be prepared analogously according to procedures well known in the art. For example, preparative syntheses of compounds of formula (5a) are taught by C. R. Schmidt et al., *Bioorg. Med. Chem. Lett.* 9 (1999) 523–528.

All solvents were ACS grade and were used as supplied. All reagents were commercially available and used without furter purification unless otherwise noted. LCMS data was recorded on a Hewlett Packard 1100 series instrument. The method used was 5% acetonitrile—95% water (0.05% TFA) to 95% acetonitrile—5% water (0.05% TFA) over two minutes and hold for three minutes on a Waters Symmetry C18 2.1×50 mm column at 35° C. $^1$H NMR spectra were recorded at 400 MHz on a Varian 400 spectrometer unless otherwise noted.

Preparation 1

[6-Methoxy-2-(2-methoxy-benzyl)-benzo[b]thiophen-3-yl]-[4-(2-piperidin-1-yl-ethoxy)-phenyl]-methanone

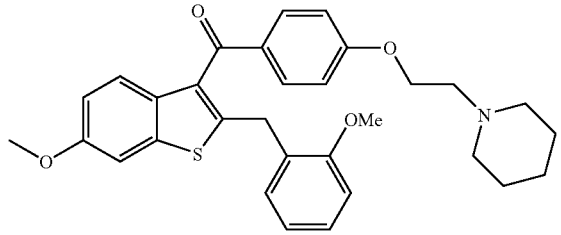

Add a solution of 2-methoxybenzylmagnesium chloride (5 mL of 0.25 M/THF) to a stirred solution of (2-dimethylamino-6-methoxy-benzo[b]thiophen-3-yl)-[4-(2-piperidin-1-yl-ethoxy)-phenyl]-methanone (500 mg, 1.14 mmol) in THF (5 mL) at −78° C. After 30 min, add additional 2-methoxybenzyl-magnesium chloride (5 mL). After 30 min, quench with water and dilute with iPrOH/CHCl$_3$(1:3). Wash the organic phase with water and brine, dry over MgSO$_4$, filter and concentrate to yield 6-methoxy-2-(2-methoxy-benzyl)-benzo[b]thiophen-3-yl]-[4-(2-piperidin-1-yl-ethoxy)-phenyl]-methanone (686 mg). Use the crude product without further purification.

$^1$H NMR (CDCl$_3$): 7.85 (d, J=9.3 Hz, 2H), 7.28 (t, J=8.8 Hz, 1H), 7.19 (m, 3H), 6.93 (d, J=9.3 Hz, 2H), 6.82–6.87 (m, 2H), 6.78 (d, J=8.3 Hz, 1H), 4.17 (m, 4H), 3.81 (s, 3H), 3.66 (s, 3H), 2.80 (t, J=5.9 Hz, 2H), 2.52 (br. S, 4H), 1.62 (m, 4H), 1.45 (m, 2H). LCMS: 3.14 min, m/z=516 (M+H)$^+$ Preparation 2

[6-Hydroxy-2-(2-hydroxy-benzyl)-benzo[b]thiophen-3-yl]-[4-(2-piperidin-1-yl-ethoxy)-phenyl]-methanone

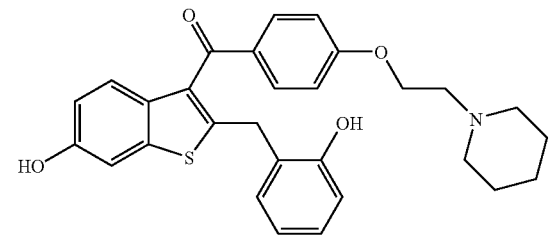

Prepare the HCl salt of [6-methoxy-2-(2-methoxy-benzyl)-benzo[b]thiophen-3-yl]-[4-(2-piperidin-1-yl-ethoxy)-phenyl]-methanone by adding sat. HCl/Ether to a solution in CH$_2$Cl$_2$. Concentrate to dryness and redissolve in CH$_2$Cl$_2$ (5 mL). Cool this solution to 0° C. and add BBr$_3$ (1 mL). Stir for 2 h while warming to r.t. Quench the reaction with sat. NaHCO$_3$ and dilute with i-PrOH/CHCl$_3$ (1:3). Wash the organic phase with water and brine, dry over MgSO$_4$, filter and concentrate. Purify the crude by flash chromatography (0–5% (2M NH$_3$ in MeOH)/CH$_2$Cl$_2$) to afford [6-hydroxy- 2-(2-hydroxy-benzyl)-benzo[b]thiophen-3-yl]-[4-(2-piperidin-1-yl-ethoxy)-phenyl]-methanone (300 mg, 54%, 2 steps).

$^1$H NMR (CDCl$_3$): 7.76 (d, J=9.2 Hz, 2H), 7.13–7.25 (m, 2H), 7.00 (d, J=2.2, 1H), 6.83–6.93 (m, 3H), 6.61–6.71 (m, 3H), 4.22 (s, 2H), 4.17 (m, 2H), 2.84 (m, 2H), 2.58 (br. s, 4H), 1.63 (br. m, 4H), 1.45 (br. m, 2H).

EXAMPLE 1

5-[4-(2-Piperidin-1-yl-ethoxy)-phenyl]-5,11-dihydro-6-oxa-12-thia-dibenzo[a,f]azulen-2-ol

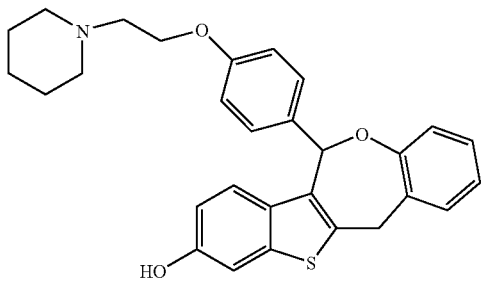

Add DIBAL solution (5 mL, 1M/THF) dropwise to [6-hydroxy-2-(2-hydroxy-benzyl)-benzo[b]thiophen-3-yl]-[4-(2-piperidin-1-yl-ethoxy)-phenyl]-methanone (300 mg, 0.6 mmol) in THF (5 mL) at −78° C. Stir for 30 min and quench with water, followed by TFA (5 mL). Stir the mixture for 3 h while warming to r.t. Remove the solvent in vacuo and dissolve the residue in i-PrOH/CH$_2$Cl$_2$ (1:3). Wash the organic phase with water and brine, dry over MgSO$_4$, filter and concentrate. Purify by flash chromatography (0–5% (2M NH$_3$ in MeOH)/CH$_2$Cl$_2$) to afford 5-[4-(2-piperidin-1-yl-ethoxy)-phenyl]-5,11-dihydro-6-oxa-12-thia-dibenzo[a,f]azulen-2-ol (180 mg, 62%).

$^1$HNMR (CDCl$_3$): 7.20 (dd, J=7.0, 1.8 Hz, 1H), 6.96–7.10 (m, 5H), 6.71 (d, J=8.1 Hz, 2H), 6.64 (d, J=8.4 Hz, 2H), 6.54 (dd, J=8.8, 2.6 Hz, 1H), 6.26 (s, 1H), 4.26 (ABq, J=15.8 Hz, 1H), 4.14 (ABq, J=16.1 Hz, 1H), 4.02 (m, 2H), 2.78 (m, 2H), 2.55 (br.s, 4H), 1.62 (br. m, 4H), 1.43 (br. m, 2H). LCMS: 2.99 min; m/z=472 (M+H)$^+$ Preparation 3

(2,6-Dimethoxy-naphthalen-1-yl)-[4-(2-piperidin-1-yl-ethoxy)-phenyl]-methanone

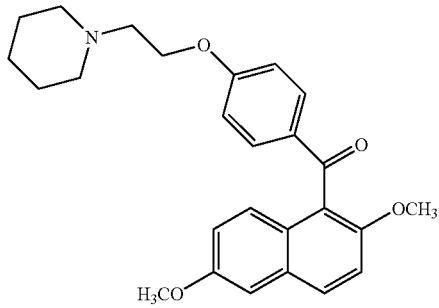

In a dry round bottom flask equipped with stir bar, temperature probe and N$_2$ line, dissolve 2,6-dimethoxynaphthalene (1.0 eq) in CH$_2$Cl$_2$ (5 volume equivalents) at ambient temperature. Cool the solution to 0° C. in with an ice bath, and add 4-(2-piperidin-1-yl-ethoxy)-benzoyl chloride (1.1 eq). Add aluminum chloride (2.0 eq). Once the reaction is determined to be complete, quench the reaction slowly with 1 N NaOH and dilute with additional water and CH$_2$Cl$_2$. Wash the aqueous layer with (1×20 mL) of CH$_2$Cl$_2$. Combine the organic extracts and wash with brine and dry (Na$_2$SO$_4$). Recrystallize the crude product from methanol to give (2,6-dimethoxy-naphthalen-1-yl)-[4-(2-piperidin-1-yl-ethoxy)-phenyl]-methanone (average yield 68%).

Preparation 4

(2-Hydroxy-6-methoxy-naphthalen-1-yl)-[4-(2-piperidin-1-yl-ethoxy)-phenyl]-methanone

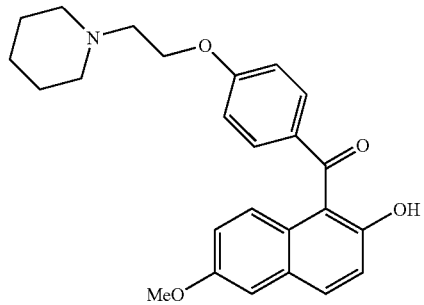

Dissolve (2,6-Dimethoxy-naphthalen-1-yl)-[4-(2-piperidin-1-yl-ethoxy)-phenyl]-methanone in CH$_2$Cl$_2$ (10 volume equivalents) in a 3-neck round bottom flask equipped with a pressure equalizing addition funnel, stirbar, and N$_2$ source. Cool the flask in an ice/brine bath and add 1.0 M BCl$_3$ solution in CH$_2$Cl$_2$ (1.2 equivalents) dropwise. The reaction solution turns dark red and the temperature initially increases to 5° C. Within one hour, all starting material is consumed, as determined by TLC (1:1, Ether:Petroleum Ether). Quench the reaction with methanol (5 equivalents) and allow to warm to room temperature. Dilute the organic solution with CH$_2$Cl$_2$ (one volume equivalent) and add to a 1.0 M NaHCO$_3$ solution (5 volume equivalents) and stir for one hour. Separate the aqueous and organic layers. Wash the aqueous layer with CH$_2$Cl$_2$ (one volume) and the combine organic layers, wash with saturated NH$_4$Cl and dry over Na$_2$SO$_4$. Purify the product via column chromatography (50/1 silica gel) eluting with CH$_2$Cl$_2$/Hexanes (3/1) to yield (2-hydroxy-6-methoxy-naphthalen-1-yl)-[4-(2-piperidin-1-yl-ethoxy)-phenyl]-methanone (typical yield 87%).

Preparation 5

Trifluoro-methanesulfonic acid 6-methoxy-1-[4-(2-piperidin-1-yl-ethoxy)-benzoyl]-naphthalen-2-yl ester

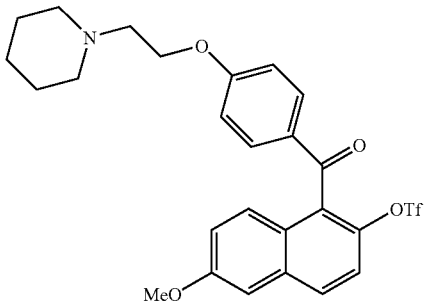

Dissolve (2-hydroxy-6-methoxy-naphthalen-1-yl)-[4-(2-piperidin-1-yl-ethoxy)-phenyl]-methanone in CH$_2$Cl$_2$ (10 volumes) in a three neck round bottom flask equipped with a stir bar and N$_2$ source and chill to 0° C. in an ice/brine bath. Add pyridine (1.3 equivalents). Add trifluoromethane sulfonyl chloride (1.2 equivalents) via syringe over 15 minutes. The yellow slurry turns clear orange with this addition. The reaction is determined to be complete by HPLC analysis after 15 minutes. Quench the reaction with H$_2$O (10 volumes), wash with 1 N HCl (5 volumes), wash with 1.0 N NaHCO$_3$, and dry over Na$_2$SO$_4$. After concentration, trifluoro-methanesulfonic acid 6-methoxy-1-[4-(2-piperidin-1-yl-ethoxy)-benzoyl]-naphthalen-2-yl ester as a clean yellow foam is obtained in quantitative yield. Use the product without further purification.

Preparation 6

[6-Methoxy-2-(2-methoxy-benzyl)-naphthalen-1-yl]-[4-(2-piperidin-1-yl-ethoxy)-phenyl]-methanone

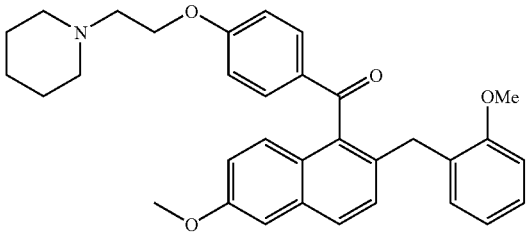

Add a solution of 2-methoxybenzylzinc chloride (8 mL, 0.5 M/THF) to a mixture of trifluoro-methanesulfonic acid 6-methoxy-1-[4-(2-piperidin-1-yl-ethoxy)-benzoyl]-naphthalen-2-yl ester (1.0 g, 1.86 mmol), Bu$_4$NI (2.1 g, 5.7 mmol), Pd(dba)$_2$ (68 mg 0.12 mmol) and dppf (66 mg, 0.12 mmol) in NMP/THF (5 mL, 3:2). Heat the mixture to reflux for 2 h. Quench the reaction with water and dilute with CH$_2$Cl$_2$. Wash the organic phase with water and brine, dry over MgSO$_4$, filter and concentrate. Load the crude product on an SCX cartridge, wash with MeOH and elute with 2M NH$_3$/MeOH. Purify the resulting product by flash chromatography (0–5% (2M NH$_3$/MeOH)/CH$_2$Cl$_2$) to afford [6-methoxy-2-(2-methoxy-benzyl)-naphthalen-1-yl]-[4-(2-piperidin-1-yl-ethoxy)-phenyl]-methanone (820 mg, 87%).

$^1$H NMR (300 MHz, CDCl$_3$): 7.77 (br. d, J=6.6 Hz, 2H), 7.69 (d, J=8.4 Hz, 1H), 7.41 (d, J=9.2 Hz, 1H), 7.26 (m, 1H), 7.13 (m, 2H), 6.98–7.03 (m, 2H), 6.76–6.93 (m, 4H), 4.17 (m, 2H), 3.91 (m, 2H), 3.89 (s, 3H), 3.69 (s, 3H), 2.81 (br. m, 2H), 2.54 (br. s, 4H), 1.63 (br. b, 4H), 1.45 (br. m, 2H).

Preparation 7

[6-Hydroxy-2-(2-hydroxy-benzyl)-naphthalen-1-yl]-[4-(2-piperidin-1-yl-ethoxy)-phenyl]-methanone

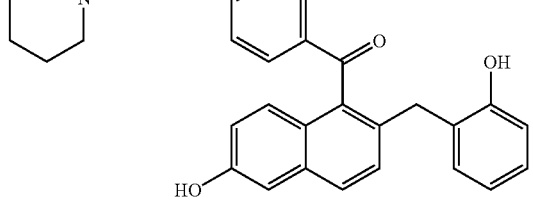

Add BBr$_3$ (0.3 mL) dropwise to a stirred solution of [6-methoxy-2-(2-methoxy-benzyl)-naphthalen-1-yl]-[4-(2-piperidin-1-yl-ethoxy)-phenyl]-methanone (650 mg, 1.28 mmol) in CH$_2$Cl$_2$ (15 mL) at room temperature. Stir for 1 h and add an additional aliquot of BBr$_3$ (0.2 mL). Continue stirring for 1 h and quench with MeOH and 2-methyl-2-butene. Load the resulting solution on an SCX cartridge, wash with MeOH and elute with 2M NH$_3$/MeOH. Purify the resulting product by flash chromatography (0–5% (2M NH$_3$ in MeOH)/CH$_2$Cl$_2$) to afford [6-hydroxy-2-(2-hydroxy-benzyl)-naphthalen-1-yl]-[4-(2-piperidin-1-yl-ethoxy)-phenyl]-methanone (161 mg, 26%).

$^1$H NMR (300 MHz, CDCl$_3$): 7.79 (br. m), 7.49 (d, J=8.8 Hz, 1H), 7.21–7.27 (m, 2H), 6.99–7.14 (m), 6.87 (dd, J=9.2, 2.6 Hz, 1H), 6.73–6.80 (m), 6.48 (br. m), 4.13 (t, J=5.9 Hz, 2H), 3.85 (ABq, 2H), 2.80 (t, J=6.2 Hz), 2.54 (br. s), 2.37–2.39 (m), 1.25–1.63 (m)

Preparation 8

6-(2-Hydroxy-benzyl)-5-{hydroxy-[4-(2-piperidin-1-yl-ethoxy)-phenyl]-methyl}-naphthalen-2-ol

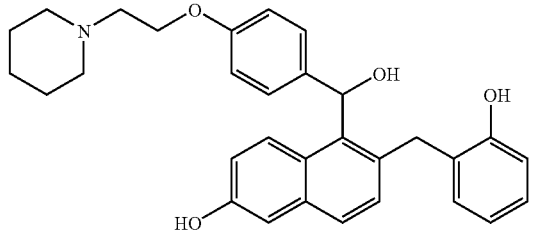

Add LAH solution (0.3 mL, 1M/THF) to a solution of [6-hydroxy-2-(2-hydroxy-benzyl)-naphthalen-1-yl]-[4-(2-piperidin-1-yl-ethoxy)-phenyl]-methanone (150 mg, 0.31 mmol) in THF (3 mL) at r.t. Stir for 30 min and quench with aq. NaHCO$_3$. Dilute with CH$_2$Cl$_2$, wash with water and brine, dry over MgSO$_4$, filter and concentrate. Purify the crude product by flash chromatography (0–5% (2M NH$_3$ in MeOH)/CH$_2$Cl$_2$) to afford 6-(2-hydroxy-benzyl)-5-{hydroxy-[4-(2-piperidin-1-yl-ethoxy)-phenyl]-methyl}-naphthalen-2-ol (123 mg, 82%).

MS: m/z=484 (M+H)$^+$

EXAMPLE 2

13-[4-(2-Piperidin-1-yl-ethoxy)-phenyl]-7,13-dihydro-12-oxa-benzo[4,5]cyclohepta[1,2-a]naphthalen-3-ol

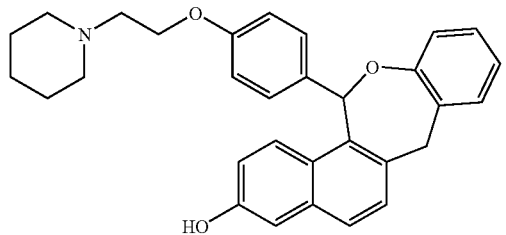

Dissolve 6-(2-hydroxy-benzyl)-5-{hydroxy-[4-(2-piperidin-1-yl-ethoxy)-phenyl]-methyl}-naphthalen-2-ol (80 mg, 0.17 mmol) in HCl solution (20% 1M aq. HCl in THF). Stir at r.t. for 2 h and warm gently for 10 min. Dilute with CH$_2$Cl$_2$, wash with sat. NaHCO$_3$, water and brine, dry over MgSO$_4$, filter and concentrate. Purify the crude product by flash chromatography (0–5% (2M NH3 in MeOH)/CH$_2$Cl$_2$) to afford 13-[4-(2-piperidin-1-yl-ethoxy)-phenyl]-7,13-dihydro-12-oxa-benzo[4,5]cyclohepta[1,2-a]naphthalen-3-ol (43 mg, 56%).

$^1$H NMR (300 MHz, CDCl$_3$): 7.47 (t, J=8.8 Hz, 2H), 7.31 (d, J=8.4 Hz, 1H), 7.20 (dd, J=7.3, 1.8 Hz, 1H), 7.02–7.08 (m, 4H), 6.94 (t, J=7.3 Hz, 1H), 6.83–6.87 (m, 3H), 6.57 (8.8 Hz, 2H), 4.50 (d, 14.6 Hz, 1H), 4.04 (m, 2H), 3.96 (d, J=14.6 Hz, 1H), 2.85 (br. m, 2H), 2.66 (br. s, 4H), 1.69 (br. m, 4H), 1.47 (br. s, 2H) LCMS: 3.00 min; m/z=466 (M+H)+

Biological Test Procedure

General Preparation Procedure

Competition binding assay is run in a buffer containing 50 mM Hepes, pH 7.5, 1.5 mM EDTA, 150 mM NaCl, 10% glycerol, 1 mg/ml ovalbumin and 5 mM DTT, using 0.025 μCi per well $^3$H-Estradiol(NEN #NET517 at 118 Ci/mmol, 1 mCi/ml), 10 ng/well ERAlpha or ERbeta receptor (PanVera). Competing compounds are added at 10 different concentrations. Non-specific binding is determined in the presence of 1 μM of 17-B Estradiol. The binding reaction (140 μl) is incubated for 4 hours at room /temperature, then 70 μl of cold DCC buffer is added to each reaction (DCC buffer contains per 50 ml of assay buffer, 0.75 g of charcoal (Sigma) and 0.25 g of dextran (Pharmacia)). Plates are mixed 8 minutes on an orbital shaker at 4° C. Plates are then centrifuged at 3,000 rpm at 4° C. for 10 minutes. An aliquot of 120 μl of the mix is transferred to another 96-well, white flat bottom plate (Costar) and 175 μl of Wallac Optiphase "Hisafe 3" scintillation fluid is added to each well. Plates are sealed and shaken vigorously on an orbital shaker. After an incubation of 2.5 hrs, read plates in a Wallac Microbeta counter. The data is used to calculate an IC50 and % Inhibition at 10 μM. The K$_d$ for $^3$H-Estradiol is determined by saturation binding to ER alpha and ER beta receptors. The IC$_{50}$ values for compounds are converted to K$_i$; using Cheng-Prusoff equation and the K$_d$ determined by saturation binding assay.

Ishikawa human endometrial tumor cells are maintained in MEM (minimum essential medium, with Earle's salts and L-Glutamine, Gibco BRL, Gaithersburg, Md.), supplemented with 10% fetal bovine serum (FBS) (VN), (Gibco BRL). One day prior to assay, growth media is changed to assay medium, DMEM/F-12 (3:1) (Dulbecco's Modified Eagle Medium: Nutrient Mixture F-12, 3:1 Mixture, phenol red-free, Gibco BRL) supplemented with 5% dextran coated charcoal stripped fetal bovine serum (DCC-FBS) (Hyclone, Logen, Utah), L-Glutamine (2 mM), MEM sodium pyruvate (1 mM), HEPES (N-[2-hydroxyethyl]piperazine-N'-[2-ethanesulfonic acid] 2 mM) all from Gibco BRL). After an overnight incubation, ishikawa cells are rinsed with Dulbecco's Phosphate Buffered Saline (1×) (D-PBS) without Ca$^{+2}$ and Mg$^{+2}$ (Gibco BRL), and trypsinized by a 3 minute incubation with 0.25% Trypsin/EDTA, phenol red-free (Gibco BRL). Cells are resuspended in assay medium and adjusted to 250,000 cells/ml. Approximately 25,000 cells in a 100 ul media are added to flat-bottom 96 wells microculture plates (Costar 3596) and incubated at 37° C. in a 5% CO$_2$ humidified incubator for 24 hours. The next day, serial dilutions of compounds are prepared in assay medium (at 6 times the final concentration in the assay). The assay is run in dual mode, agonist and antagonist modes. For the agonist mode, plates receive 25 μl/well of assay medium followed by 25 μl/well of diluted compounds (at 6× the final concentrations). For the antagonist mode, plates receive 25 μl/well of 6 nM E$_2$ (β-Estradiol, Sigma, St. Louis, Mo.) followed by 25 μl/well of diluted compounds (at 6× the final concentrations). After an additional 48-hour incubation at 37° C. in a 5% CO$_2$ humidified incubator, media is aspirated from wells and 100 μl fresh assay medium is added to each microculture. Serial dilutions of compounds are prepared and added to the cells as described above. After an additional 72 hour incubation at 37° C. in a 5% CO$_2$ humidified incubator, the assay is quenched by removing media and rinsing plates twice in Dulbecco's Phosphate Buffered Saline (1×) (D-PBS) (Gibco BRL). The plates are dried for 5 min and frozen at −70° C. for at least 1 hour. The plates are then removed from the freezer and allowed to thaw at room temperature. To each well, 100 μl of 1-Step™ PNPP (Pierce Chemical Company, Rockford, Ill.) is added. After a 20-minute incubation, plates are read on a spectophotometer at 405 nm. The data is fitted to a linear interpolation to derive EC50 (for agonist mode) or IC50 (for antagonist mode) values. For the agonist mode, a % efficacy for each compound is calculated versus the response to Tamoxifen. For the antagonist mode, a % efficacy for each compound is calculated versus E2 (1 nM) alone.

MCF-7 breast adenocarcinoma cells (ATCC HTB 22) are maintained in MEM (minimal essential medium, phenol red-free, Gibco BRL) supplemented with 10% fetal bovine serum (FBS) (V/V), L-glutamine (2 mM), sodium pyruvate (1 mM), HEPES ((N-[2-hydroxyethyl]piperazine-N'-[2-ethanesulfonic acid]10 mM}, non-essential amino acids (0.1 mM) and Penicillin Streptomycin (1×). Seven days prior to assay, MCF-7 cells are switched to assay media which is the same as maintenance medium except supplemented with 10% dextran-coated charcoal-stripped fetal bovine serum (DCC-FBS) assay medium in place of 10% FBS. MCP-7 cells are removed from flasks using 10× *Trypsin* EDTA (*phenol* red *free*, *Gibco* BRL) and diluted to 1× in (Ca++/Mg++ free HBSS (phenol red-free). Cells are adjusted to 80,000 cells/ml in assay medium. Approximately 8,000 cells (100 μl) are added to each well in 96 well Cytostar T scintillation plates (Amersharn) and incubated at 37° C. in a 5% $CO_2$ humidified incubator for 24 hours to allow cell adherence and equilibration after transfer. Serial dilutions of drugs are prepared in assay medium at 4× the final desired concentration). A 50 μl aliquot of drug dilutions (at 4× the final assay concentration) is transferred to duplicate wells followed by 50 μl assay medium for the agonist mode or 50 μl of 40 pM of E2 for the antagonist mode to a final volume of 200 μl. For each of the agonist plates, a basal level (media) and a maximum stimulated level (with 1 μM E2) is determined. For each of the antagonist plates, a basal level (media) and a E2 (10 pM) alone control is determined. After an additional 48 hours at 37° C. in a 5% $CO_2$ humidified incubator, 20 μl of assay medium containing 0.01 μCi of $^{14}C$-thymidine (52 mCi/mmol, 50 μCi/ul, Amersham) is added to each well. The plates are incubated overnight in the same incubator and then counted on the Wallac Microbeta counter. The data is averaged to calculate an IC50 and % inhibition @ 1 M for the antagonist mode. For the agonist mode, an EC50 and percent of maximum E2 stimulation and concentration of maximum stimulation is calculated.

TABLE

| | ER binding | | MCF-7 | | | |
|---|---|---|---|---|---|---|
| | $K_i$ | $K_i$ | MCF-7 | Ishikawa | | |
| Cmpnd (Ex. No.) | (ERα) (nM) | (ERβ) (nM) | IC50 (nM) | Ishikawa EC50 (nM) | Agonist % Eff | IC50 (nM) |
| 1 | 1 | 1 | 8 | N/D | 4 | 19 |
| 2 | 2 | 3 | 10 | N/D | 24 | 454 |

General Rat Preparation Procedure

Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with a compound of formula (I) ("F—I") is initiated. 17α-ethynyl estradiol or F—I is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH –8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from these animals are also scanned by quantitative computed tomography. In accordance with the above procedures, F—I or ethynyl estradiol ($EE_2$) in 20% hydroxypropyl β-cyclodextrin are orally administered to test animals. F—I is also useful in combination with estrogen or progestin.

Uterine Fibrosis Test Procedures

Test 1: Between 3 and 20 women having uterine fibrosis are administered F—I. The amount of compound administered is from 0.1 to 1000 mg/day, and the period of administration is 3 months. The women are observed during the period of administration, and up to 3 months after discontinuance of administration, for effects on uterine fibrosis.

Test 2: The same procedure is used as in Test 1, except the period of administration is 6 months.

Test 3: The same procedure is used as in Test 1, except the period of administration is 1 year.

Test 4: Prolonged estrogen stimulation is used to induce leiomyomata in sexually mature female guinea pigs. Animals are dosed with estradiol 3–5 times per week by injection for 2–4 months or until tumors arise. Treatment consisting of F—I or vehicle is administered daily for 3–16 weeks and then animals are sacrificed and the uteri harvested and analyzed for tumor regression.

Test 5: Tissue from human leiomyomas are implanted into the peritoneal cavity and/or uterine myometrium of sexually mature, castrated, female, nude mice. Exogenous estrogen is supplied to induce growth of the explanted tissue. In some cases, the harvested tumor cells are cultured in vitro prior to implantation. Treatment consisting of F—I or vehicle is supplied by gastric lavage on a daily basis for 3–16 weeks and implants are removed and measured for growth or regression. At the time of sacrifice, the uteri are harvested to assess the status of the organ.

Test 6: Tissue from human uterine fibroid tumors is harvested and maintained, in vitro, as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F—I, and vehicle. Levels of steroid hormone receptors are assessed weekly to determine whether important cell characteristics are maintained in vitro. Tissue from 5–25 patients is utilized.

Test 7: F—I's ability to inhibit estrogen-stimulated proliferation of leiomyoma-derived ELT cell lines is measured substantially as described in Fuchs-Young, et al., "Inhibition of Estrogen-Stimulated Growth of Uterine Leiomyomas by Selective Estrogen Receptor Modulators", Mol. Car., 17(3): 151–159 (1996), the teachings of which are herein incorporated by reference.

Endometriosis Test Procedures

Test 1: Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed. On the day following surgery, animals in Groups 1 and 2 receive intraperitoneal injections of water for 14 days whereas animals in Group 3 receive intraperitoneal injections of 1.0 mg of F—I per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2: Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. Approximately 50 days following surgery, animals assigned to Group 1 receive intraperitoneal injections of water for 21 days whereas animals in Group 2 receive intraperitoneal injections of 1.0 mg of F—I per kilogram of body weight for the same duration. Following 21 days of treatment, each female is sacrificed and the endometrial explants and adrenals are removed and weighed. The explants are measured as an indication of growth. Estrous cycles are monitored.

Test 3: Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

Test 4: Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of F—I supplied by gastric lavage on a daily basis for 3–16 weeks, and implants are removed and measured for growth or regression. At the time of sacrifice, the uteri are harvested to assess the status of the intact endometrium.

Test 5: Tissue from human endometrial lesions is harvested and maintained ill vitro as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F—I, and vehicle. Levels of steroid hormone receptors are assessed weekly to determine whether important cell characteristics are maintained in vitro. Tissue from 5–25 patients is utilized.

Use of Formula (I Compound in Conjunction with Estrogen

Peri- and post-menopausal women often undergo hormone replacement therapy (HRT) to combat negative consequences associated with the drop in circulating endogenous estrogen, e.g., to treat hot flashes. However, HRT has been associated with increased risks of certain cancers including uterine and breast cancer. F—I may be employed in conjunction with HRT to inhibit these risks.

Prevention of Breast Cancer

This invention also relates to the administration of F—I to a recipient who is at risk of developing de novo breast cancer. The term "de novo", as used herein, means the lack of transformation or metamorphosis of normal breast cells to cancerous or malignant cells in the first instance. Such a transformation may occur in stages in the same or daughter cells via an evolutionary process or may occur in a single, pivotal event. This de novo process is in contrast to the metastasis, colonization, or spreading of already transformed or malignant cells from the primary tumor site to new locations.

A person who is at no particular risk of developing breast cancer is one who may develop de novo breast cancer, has no evidence or suspicion of the potential of the disease above normal risk, and who has never had a diagnosis of having the disease. The greatest risk factor contributing to the development of breast carcinoma is a personal history of suffering from the disease, or an earlier occurrence of the disease, even if it is in remission with no evidence of its presence. Another risk factor is family history of the disease.

Induction of mammary tumors in rats by administration of the carcinogen N-nitroso-N-methylurea is a well-accepted animal model for the study of breast cancer and has been found suitable for analyzing the effect of chemopreventive agents.

In two separate studies, 55-day old female Sprague-Dawley rats are given an intravenous (Study 1) or intraperitoneal (Study 2) dose of 50 mg of N-nitroso-N-methylurea per kilogram of body weight one week prior to feeding ad libitum a diet into which varying amounts of F—I, (Z)-2-[4-(1,2-diphenyl-1-butenyl)phenoxy]-N,N-dimethylethanamine base (tamoxifen base), or control are blended.

In Study 1, the dietary doses of 60 mg/kg of diet and 20 mg/kg of diet translates into roughly comparable doses of 3 and 1 mg/kg of body weight for the test animals.

In Study 2, the dietary doses of 20, 6, 2, and 0.6 mg/kg of diet translates roughly into comparable doses of 1, 0.3, 0.1 and 0.03 mg/kg of body weight for the test animals.

Rats are observed for evidence of toxicity and are weighed and palpated for tumor formation once a week. The animals are sacrificed after thirteen weeks (Study 1) or eighteen weeks (Study 2) and tumors are confirmed and weighed at autopsy.

Therapeutic Methods of Use and Dosages

The present invention also provides a method of inhibiting a disease associated with estrogen deprivation and a method for inhibiting a disease associated with an aberrant physiological response to endogenous estrogen which comprises the aforementioned method using compounds of Formula I and optionally comprises administering to a patient an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin®, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "patient" refers to a warm-blooded animal or mammal which is in need of inhibiting a disease associated with estrogen deprivation or in need of inhibiting a disease associated with an aberrant physiological response to endogenous estrogen. It is understood that guinea pigs, dogs, cats, rats, mice, hamsters, and primates, including humans, are examples of patients within the scope of the meaning of the term. Preferred patients include humans. Most preferred patients include postmenopausal female humans.

As used herein, the term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

The term "estrogen deprivation" is meant to imply the condition where the optimal level of estrogen is absent. This level varies from one tissue to another depending on the function of the tissue. Thus, in some cases, estrogen deprivation may be the total absence of estrogen, whereas in other cases, deprivation may involve estrogen levels which are too low for proper tissue function. In human women, the two most common causes of estrogen deprivation are menopause and ovariectomy, although other conditions can be causative. Estrogen deprivation can lead to conditions including osteoporosis and cardiovascular effects such as hyperlipidemia, proliferation of aortal smooth muscle cells (restenosis), decrease in nitric oxide production (hypertension) and decrease in production of the enzyme PAI-1 (Plasminogen Activator Inhibitor-1), i.e. thrombosis.

Reduction or amelioration of other pathologies associated with menopause such as urinary incontinence, vaginal dryness, increase in the incidence of auto-immune disease, and loss of skin tone, may also be achieved by administering compounds of Formula I.

In addition to their usefulness in treating conditions associated with estrogen deprivation following menopause, the compounds of the present invention are also useful in the treatment of disease states associated with inappropriate response to endogenous estrogen in tissues both prior to and subsequent to menopause.

One example of a pathological condition associated with abnormal cellular responses to endogenous estrogen in tissues is estrogen dependent breast cancer. Estrogen dependent breast tumor cells proliferate in the presence of estrogen and the treatment of this disease has been to stop all action of estrogen on these cells.

Another estrogen dependent pathology is uterine fibrosis (uterine fibroid disease). Essentially, uterine fibrosis is a condition where there is a deposition of fibroid tissue on the wall of the uterus. This condition is a cause of dysmenorrhea and infertility in women. The exact cause of this condition is poorly understood but evidence suggests that it is an inappropriate response of fibroid tissue to estrogen. The most common treatment of uterine fibrosis involves surgical procedures both costly and sometimes a source of complications such as the formation of abdominal adhesions and infections.

Yet another disease in this category is endometriosis, a condition of severe dysmenorrhea, which is accompanied by severe pain, bleeding into the endometrial masses or peritoneal cavity and often leads to infertility. The cause of the symptoms of this condition appear to be ectopic endometrial growths located in inappropriate tissues which respond inappropriately to hormonal control.

As used herein, the term "therapeutically effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose for human use will contain a nontoxic dosage level of from about 1 mg to about 600 mg/day of a compound of the present invention. Preferred daily doses generally will be from about 15 mg to about 300 mg/day. Most preferred doses range may range from 20 mg to about 100 mg, administered once to three times per day.

The compounds of this invention can be administered by a variety of routes including oral, rectal, transdermal, subcutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients; For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxyxnethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation.

I claim:
1. A compound of the formula

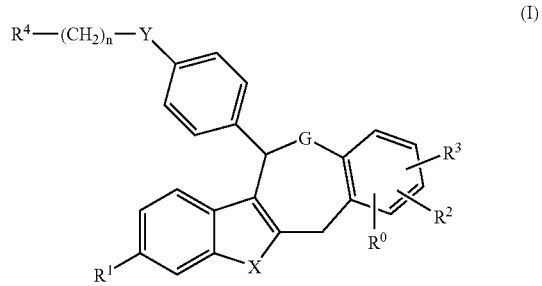

(I)

wherein
R$^1$ is —H, —OH, —O(C$_1$–C$_4$ alkyl), —OCOC$_6$H$_5$, —OCO(C$_1$–C$_6$ alkyl), or —OSO$_2$(C$_2$–C$_6$ alkyl);
R$^0$, R$^2$ and R$^3$ are each independently —H, —OH, —O(C$_1$–C$_4$ alkyl), —OCOC$_6$H$_5$, —OCO(C$_1$–C$_6$ alkyl), —OSO$_2$(C$_2$–C$_6$ alkyl) or halo;
R$^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 2 or 3;
X is —S— or —HC=CH—;
G is —O—, —S—, —SO—, SO$_2$, or —N(R$^5$)—, wherein R$^5$ is —H or C$_1$–C$_4$ alkyl; and
Y is —O—, —S—, —NH—, —NMe-, or —CH$_2$—;
or a pharmaceutically acceptable salt thereof.

2. A compound of claim 1 of the formula

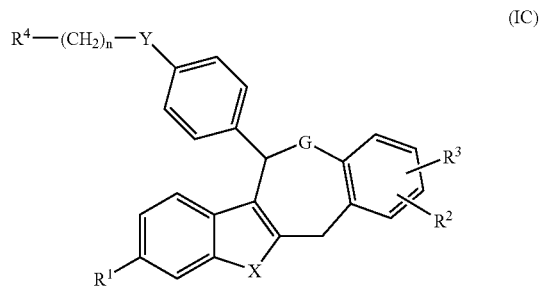

(IC)

wherein
R$^1$ is —H, —OH, —O(C$_1$–C$_4$ alkyl), —OCOC$_6$H$_5$, —OCO(C$_1$–C$_6$ alkyl), or —OSO$_2$(C$_2$–C$_6$ alkyl);
R$^2$ and R$^3$ are each independently —H, —OH, —O(C$_1$–C$_4$ alkyl), —OCOC$_6$H$_5$, —OCO(C$_1$–C$_6$ alkyl), —OSO$_2$(C$_2$–C$_6$ alkyl) or halo;
R$^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 2 or 3;
X is —S— or —HC=CH—;
G is —O—, —S—, —SO—, SO$_2$, or —N(R$^5$)—, wherein R$^5$ is —H or C$_1$–C$_4$ alkyl; and
Y is —O—, —S—, —NH—, —NMe-, or —CH$_2$—;
or a pharmaceutically acceptable salt thereof.

3. A compound according to claim 2 wherein G is —O—.
4. A compound according to claim 3 wherein Y is —O—.
5. A compound according to claim 4 wherein n is 2.

6. A compound according to claim 5 wherein $R^1$ is —OH or —OCH$_3$.

7. A compound according to claim 6 wherein $R^1$ is —OH.

8. A compound according to claim 7 wherein $R^4$ is 1-piperidinyl or 1-pyrrolidinyl.

9. A compound according to claim 8 wherein $R^4$ is 1-piperidinyl.

10. A compound according to claim 9 wherein two of $R^0$, $R^2$ and $R^3$ is —H.

11. A compound according to claim 9 wherein two of $R^0$, $R^2$ and $R^3$ is —H and the other is —OH.

12. A compound according to claim 9 wherein all of $R^0$, $R^2$ and $R^3$ are —H.

13. A compound according to claim 9 wherein at least one of $R^0$, $R^2$, and $R^3$ is halo and the other or others is —H.

14. A compound according to claim 13 wherein X is —S—.

15. A compound according to claim 13 wherein X is —HC=CH—.

16. A compound according to claim 1 wherein said compound is 5-[4-(2-piperidin-1-yl-ethoxy)-phenyl]-5,11-dihydro-6-oxa-12-thia-dibenzo[a,f]azulen-2-ol or a pharmaceutically acceptable salt thereof.

17. A compound according to claim 1 wherein said compound is 13-[4-(2-piperidin-1-yl-ethoxy)-phenyl]-7,13-dihydro-12-oxa-benzo[4,5]cyclohepta[1,2-a]naphthalen-3-ol or a pharmaceutically acceptable salt thereof.

18. A pharmaceutical composition comprising a compound according to claim 1 or a pharmaceutically acceptable salt thereof, and optionally an effective amount of estrogen and progestin, in combination with a pharmaceutically acceptable salt, diluent, or excipient.

* * * * *